(12) United States Patent
Inghardt et al.

(10) Patent No.: US 7,056,907 B2
(45) Date of Patent: Jun. 6, 2006

(54) MANDELIC ACID DERIVATIVES AND THEIR USE AS THROMBIN INHIBITORS

(75) Inventors: Tord Inghardt, Mölndal (SE); Anders Johansson, Mölndal (SE); Arne Svensson, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/487,805

(22) PCT Filed: Aug. 30, 2002

(86) PCT No.: PCT/SE02/01557

§ 371 (c)(1),
(2), (4) Date: Feb. 26, 2004

(87) PCT Pub. No.: WO03/018551

PCT Pub. Date: Mar. 6, 2003

(65) Prior Publication Data

US 2004/0242492 A1 Dec. 2, 2004

(30) Foreign Application Priority Data

Aug. 30, 2001 (SE) .................................. 0102921

(51) Int. Cl.
*C07D 205/04* (2006.01)
*A61K 31/397* (2006.01)
(52) U.S. Cl. ........................ 514/210.02; 514/210.17; 548/952; 548/953

(58) Field of Classification Search ........... 514/210.02; 548/523, 952
See application file for complete search history.

(56) References Cited

U.S. PATENT DOCUMENTS

| 6,051,568 | A  | * | 4/2000 | Gustafsson et al. .... 514/210.17 |
| 6,599,894 | B1 | * | 7/2003 | Inghardt et al. ....... 514/210.02 |
| 2004/0019033 | A1 | | 1/2004 | Inghardt et al. |

FOREIGN PATENT DOCUMENTS

| WO | WO-97/02284 | 1/1997 |
| WO | WO-00/42059 | 7/2000 |
| WO | WO-02/14270 | 2/2002 |

OTHER PUBLICATIONS

U.S. Appl. No. 10/432,411.*

* cited by examiner

*Primary Examiner*—Kamal A. Saeed
*Assistant Examiner*—Susannah Chung
(74) *Attorney, Agent, or Firm*—Fish & Neave IP Group; Ropes & Gray LLP

(57) ABSTRACT

There is provided a compound of formula (1) and pharmaceutically-acceptable derivatives (including prodrugs) thereof. Which compound and derivatives are useful as, or are as useful as prodrugs of, competitive inhibitors of trypsin-like proteases, such as thrombin, and thus in particular, in the treatment of conditions where inhibition of thrombin is required (e.g. thrombosis) or as anticoagulants.

5 Claims, No Drawings

MANDELIC ACID DERIVATIVES AND THEIR USE AS THROMBIN INHIBITORS

RELATED APPLICATIONS

This application is a national stage filing under 35 U.S.C. 371 of International Application PCT/SE02/01557, filed Aug. 30, 2002, which claims priority from Sweden Application No. 0102921-4, filed Aug. 30, 2001, the specifications of each of which are incorporated by reference herein. International Application PCT/SE02/01557 was published under PCT Article 21(2) in English.

FIELD OF THE INVENTION

This invention relates to novel pharmaceutically useful compounds, in particular compounds that are, and/or compounds that are metabolised to compounds which are, competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would be expected to exhibit antithrombotic activity. In addition, antithrombotic activity would be expected to be enhanced by effective inhibition of the positive feedback mechanism.

PRIOR ART

The early development of low molecular weight inhibitors of thrombin has been described by Claesson in Blood Coagul. Fibrinol. (1994) 5, 411.

Blombäck et al (in J. Clin. Lab. Invest. 24, suppl. 107, 59, (1969)) reported thrombin inhibitors based on the amino acid sequence situated around the cleavage site for the fibrinogen Aα chain. Of the amino acid sequences discussed, these authors suggested the tripeptide sequence Phe-Val-Arg (P9-P2-P1, hereinafter referred to as the P3-P2-P1 sequence) would be the most effective inhibitor.

Thrombin inhibitors based on dipeptidyl derivatives with an α,ω-aminoalkyl guanidine in the P1-position are known from U.S. Pat. No. 4,346,078 and International Patent Application WO 93/11152. Similar, structurally related, dipeptidyl derivatives have also been reported. For example International Patent Application WO 94/29336 discloses compounds with, for example, aminomethyl benzamidines, cyclic aminoalkyl amidines and cyclic aminoalkyl guanidines in the P1-position (International Patent Application WO 97/23499 discloses prodrugs of certain of these compounds); European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidino-piperidine) in the P1-position are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported. For example, International Patent Application WO 93/18060 discloses hydroxy acids, European Patent Application 0 526 877 des-amino acids, and European Patent Application 0 542 525 O-methyl mandelic acids in the P3-position.

Inhibitors of serine proteases (e.g. thrombin) based on electrophilic ketones in the P1-position are also known. For example, European Patent Application 0 195 212 discloses peptidyl α-keto esters and amides, European Patent Application 0 362 002 fluoroalkylamide ketones, European Patent Application 0 364 344 α,β,δ-triketocompounds, and European Patent Application 0 530 167 α-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on peptidyl derivatives have been disclosed in European Patent Application 0 669 317 and International Patent Applications WO 95/35309, WO 95/23609, WO 96/25426, WO 97/02284, WO 97/46577, WO 96/32110, WO 96/31504, WO 96/03374, WO 98/06740, WO 97/49404, WO 98/57932, WO 99/29664, WO 00/35869 and WO 00/42059.

In particular, WO 97/02284 and WO 00/42059 disclose thrombin inhibitors with substituted mandelic acids in the P3 position.

However, there remains a need for effective inhibitors of trypsin-like serine proteases, such as thrombin. There is also a need for compounds which to have a favourable pharmacokinetic profile and are selective in inhibiting thrombin over other serine proteases, in particular those involved in haemostasis. Compounds which exhibit competitive inhibitory activity towards thrombin would be expected to be especially useful as anticoagulants and therefore in the therapeutic treatment of thrombosis and is related disorders.

DISCLOSURE OF THE INVENTION

According to the invention there is provided a compound of formula I

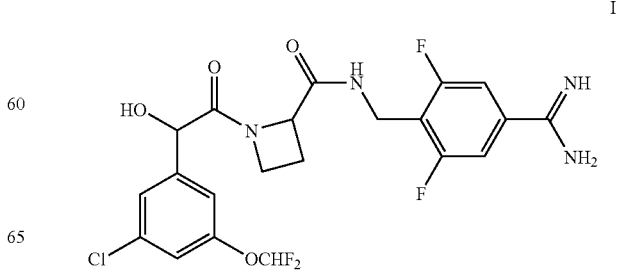

I (i.e. Ph(3-Cl)(5-OCHF$_2$)—CH(OH)C(O)-Aze-Pab(2,6-diF)), or a pharmaceutically-acceptable derivative thereof.

The term "pharmaceutically-acceptable derivative" includes pharmaceutically-acceptable salts (e.g. acid addition salts).

Abbreviations are listed at the end of this specification.

The compound of formula I may be made in accordance with techniques well known to those skilled in the art, for example as described hereinafter.

According to a further aspect of the invention there is provided a process for the preparation of the compound of formula I, which comprises:

(i) the coupling of a compound of formula II,

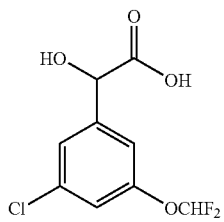

II with a compound of formula III,

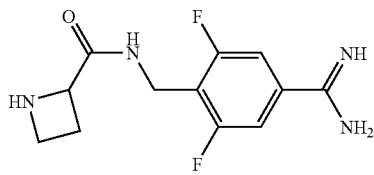

III for example in the presence of a coupling agent (e.g. oxalyl chloride in DMF, EDC, DCC, HBTU, HATU, PyBOP or TBTU), an appropriate base (e.g. pyridine, DMAP, TEA, 2,4,6-collidine or DIPEA) and a suitable organic solvent (e.g. dichloromethane, acetonitrile, EtOAc or DMF);

(ii) the coupling of a compound of formula IV,

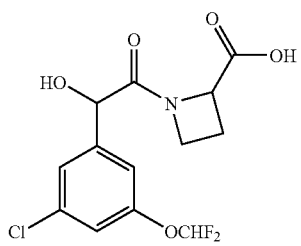

IV with the compound of formula V,

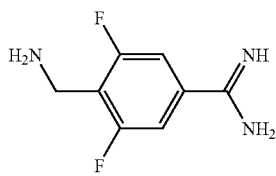

V for example under conditions as described in process (i) above; or (iii) reaction of a corresponding compound of formula XVI, as defined hereinafter, with a suitable source of ammonia (e.g. ammonium acetate or ammonia gas) under conditions known to those skilled in the art, such as by reaction of an ethylimidoate intermediate (formed by reaction of a compound of formula XVI with HCl(g) in ethanol) with ammonia gas in ethanol, or under those conditions described in *Tetrahedron Lett.* 40, 7067 (1999), the disclosures in which document are hereby incorporated by reference.

Compounds of formula II are available using known and/or standard techniques.

For example, compounds of formula II may be prepared by reaction of the aldehyde of formula VI,

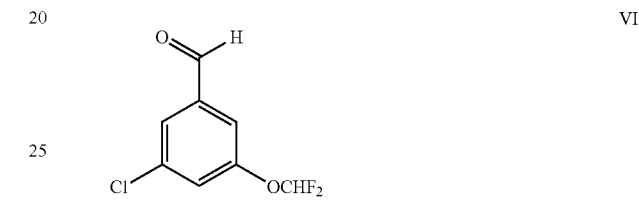

VI with:

(a) a compound of formula VII,

R"CN         VII wherein R" represents H or (CH$_3$)$_3$Si, for example at room, or elevated, temperature (e.g. below 100° C.) in the presence of a suitable organic solvent (e.g. chloroform or methylene chloride) and, if necessary, in the presence of a suitable base (e.g. TEA) and/or a suitable catalyst system (e.g. benzylammonium chloride or zinc iodide, or using a chiral catalyst, for example as described in *Chem. Rev.*, (1999) 99, 3649), followed by hydrolysis under conditions that are well known to those skilled in the art (e.g. as described hereinafter);

(b) NaCN or KCN, for example in the presence of NaHSO$_3$ and water, followed by hydrolysis;

(c) chloroform, for example at elevated temperature (e.g. above room temperature but below 100° C.) in the presence of a suitable organic solvent (e.g. chloroform) and, if necessary, in the presence of a suitable catalyst system (e.g. benzylammonium chloride), followed by hydrolysis;

(d) a compound of formula VIII,

VIII wherein M represents Mg or Li, followed by oxidative cleavage (e.g. ozonolysis or osmium or ruthenium catalysed) under conditions which are well known to those skilled in the art; or (e) tris(methylthio)methane under conditions which are well known to those is skilled in the art, followed by hydrolysis in the presence of e.g. HgO and HBF$_4$.

Compounds of formula II may alternatively be prepared by oxidation of a compound of formula IX,

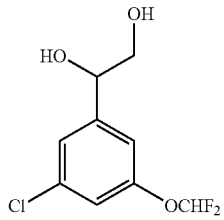

or a derivative thereof that is optionally protected at the secondary hydroxyl group, in the presence of a suitable oxidising agent (e.g. a combination of a suitable free radical oxidant (such as TEMPO) and an appropriate hypochlorite salt (such as sodium hypochlorite)) under conditions known to those skilled in the art, for example at between −10° C. and room temperature, in the presence of a suitable solvent (e.g. water, acetone or a mixture thereof), an appropriate salt (e.g. an alkali metal halide such as potassium bromide) and a suitable base (e.g. an alkali metal carbonate or hydrogen carbonate such as sodium hydrogen carbonate).

Enantiomerically-pure forms of compounds of formula II (i.e. those compounds having different configurations of substituents about the C-atom α- to the $CO_2H$ group) may be separated by an enantiospecific derivatisation step. This may be achieved, for example by an enzymatic process. Such enzymatic processes include, for example, transesterification of the α-OH group at between room and reflux temperature (e.g. at between 45 and 65° C.) in the presence of a suitable enzyme (e.g. Lipase PS Amano), an appropriate ester (e.g. vinyl acetate) and a suitable solvent (e.g. methyl tert-butyl ether). The derivatised isomer may then be separated from the unreacted isomer by conventional separation techniques (e.g. chromatography).

Groups added to compounds of formula II in such a derivatisation step may be removed either before any further reactions or at any later stage in the synthesis of compounds of formula I. The additional groups may be removed using conventional techniques (e.g. for esters of the α-OH group, hydrolysis under conditions known to those skilled in the art (e.g. at between room and reflux temperature in the presence of a suitable base (e.g. NaOH) and an appropriate solvent (e.g. MeOH, water or mixtures thereof))).

Compounds of formula III may be prepared by coupling azetidine-2-carboxylic acid to a compound of formula V, as hereinbefore defined, for example under similar conditions to those described herein for preparation of compounds of formula I.

Compounds of formula IV may be prepared by coupling a compound of formula II as hereinbefore defined to azetidine-2-carboxylic acid, for example under similar conditions to those described herein for preparation of compounds of formula I.

The compound of formula VI is available using known and/or standard techniques. For example, it may be prepared by:

(i) metallation (wherein the metal may be, for example, an alkali metal such as Li or, preferably, a divalent metal such as Mg) of a compound of formula X,

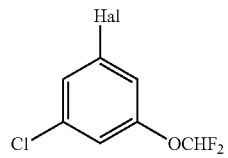

wherein Hal represents a halogen atom selected from Cl, Br and I, followed by reaction with a suitable source of the formyl group (such as N,N-dimethylformamide), for example under conditions described hereinafter;

(ii) reduction of a compound of formula XI,

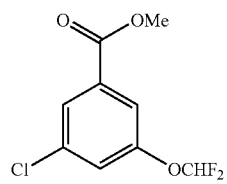

in the presence of a suitable reducing agent (e.g. DIBAL-H); or (iii) oxidation of a compound of formula XII,

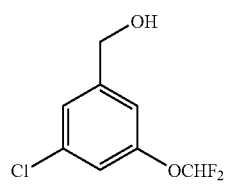

in the presence of a suitable oxidising agent (e.g. $MnO_2$, pyridinium chlorochromate, a combination of DMSO and oxalyl chloride, or $SO_3$ pyridine complex in DMSO).

Compounds of formula IX may be prepared by dihydroxylation of a corresponding compound of formula XIII

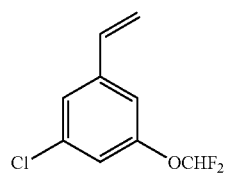

in the presence of a suitable dihydroxylating agent (e.g. a reagent or reagent mixture that provides $OsO_4$, such as AD-mix-α or, particularly, AD-mix-β), for example under conditions known to those skilled in the art, such as at between −10° C. and room temperature in the presence of an appropriate solvent (e.g. water, tert-butanol or a mixture thereof). When asymmetric oxidants such as AD-mix-α or AD-mix-β are employed, this method may be used to prepare compounds of formula IX that have specific configurations of groups (i.e. R or S) about both of the C-atoms to which the primary and secondary hydroxyl groups are attached.

The compound of formula XIII may be prepared by reaction of a corresponding compound of formula X, as hereinbefore defined, with a suitable source of the vinyl anion (e.g. tributyl(vinyl)tin) under conditions known to those skilled in the art, for example at between room and reflux temperature (e.g. 50° C.) in the presence of an appropriate solvent (e.g. toluene), a suitable coupling agent (e.g. a palladium(0) co-ordination complex such as tetrakis (triphenylphosphine)palladium(0)) and optionally in the presence of an appropriate catalyst (e.g. 2,6-di-tert-butyl-4-methylphenol).

Compounds of formulae V, VII, VIII, X, XI, XII and azetidine-2-carboxylic acid are either commercially available, are known in the literature, or may be obtained either by analogy with the processes described herein, or by conventional synthetic procedures, in accordance with standard techniques, from readily available starting materials using appropriate reagents and reaction conditions. Compounds of formula XVI may be obtained by processes described hereinafter.

Substituents on the phenyl ring in compounds of formulae I, II, III, IV, V, VI, IX, X, XI, XII and XIII may be introduced using techniques well known to those skilled in the art by way of standard functional groups interconversions, in accordance with standard techniques, from readily available starting materials using appropriate reagents and reaction conditions.

For example, compounds of formulae I, II, IV, VI, X, XI and XII may be prepared from compounds corresponding to those compounds, in which, in place of the —OCHF$_2$ group, an —OH groups is present (hereinafter referred to as "the relevant phenol precursor compounds"), for example by reaction of such a relevant phenol precursor compound with an appropriate fluorinated haloalkane (such as ClCHF$_2$), e.g. at room temperature or above (e.g. at reflux) in the presence of a suitable base (e.g. potassium tert-butoxide, KOH or NaOH, for example in aqueous solution) and an appropriate organic solvent (e.g. THF, chloroform or i-propanol), for example as described hereinafter.

The skilled person will appreciate that such functional group transformations may also be carried out at an earlier stage in the overall synthesis of compounds of formulae II, IV, VI, X, XI and XII (i.e. on appropriate precursors of the relevant phenol precursor compounds). The relevant phenol precursor compounds are either commercially available, are known in the literature, or may be obtained either by analogy with the processes described herein, or by conventional synthetic procedures, in accordance with standard techniques, from readily available starting materials using appropriate reagents and reaction conditions. For example, the relevant phenol precursor compounds may be obtained by deprotection of the corresponding protected phenols (where the protecting group may be, for example, methyl, allyl, benzyl or tert-butyl) under standard conditions.

Compounds of formula I may be isolated from their reaction mixtures using conventional techniques.

In accordance with the present invention, pharmaceutically acceptable derivatives of compounds of formula I also include "protected" derivatives, and/or compounds that act as prodrugs, of compounds of formula I.

Compounds that may act as prodrugs of compounds of formula I that may be mentioned include compounds of formula Ia,

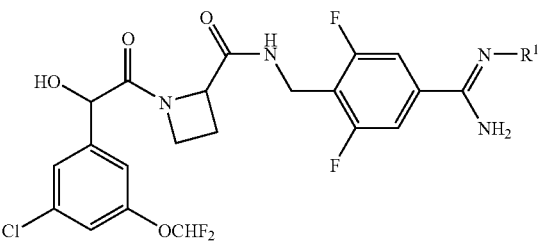

wherein $R^1$ represents $OR^2$ or $C(O)OR^3$;
$R^2$ represents H, $C_{1-10}$ alkyl, $C_{1-3}$ alkylaryl or $C_{1-3}$ alkyloxyaryl (the alkyl parts of which latter two groups are optionally interrupted by one or more oxygen atoms, and the aryl parts of which latter two groups are optionally substituted by one or more substituents selected from halo, phenyl, methyl or methoxy, which latter three groups are also optionally substituted by one or more halo substituents); and
$R^3$ represents $C_{1-10}$ alkyl (which latter group is optionally interrupted by one or more oxygen atoms), or $C_{1-3}$ alkylaryl or $C_{1-3}$ alkyloxyaryl (the alkyl parts of which latter two groups are optionally interrupted by one or more oxygen atoms, and the aryl parts of which latter two groups are optionally substituted by one or more substituents selected from halo, phenyl, methyl or methoxy, which latter three groups are also optionally substituted by one or more halo substituents), and pharmaceutically-acceptable derivatives thereof.

The term "pharmaceutically-acceptable derivatives" of compounds of formula Ia includes pharmaceutically-acceptable salts (e.g. acid addition salts).

Alkyloxyaryl groups that $R^2$ and $R^3$ may represent comprise an alkyl and an aryl group linked by way of an oxygen atom. Alkylaryl and alkyloxyaryl groups are linked to the rest of the molecule via the alkyl part of those groups, which alkyl parts may (if there is a sufficient number (i.e. three) of carbon atoms) be branched-chain. The aryl parts of alkylaryl and alkyloxyaryl groups which $R^2$ and $R^3$ may represent, or be substituted by, include carbocyclic and heterocyclic aromatic groups, such as phenyl, naphthyl, pyridinyl, oxazolyl, isoxazolyl, thiadiazolyl, indolyl and benzofuranyl and the like.

Alkyl groups which $R^2$ and $R^3$ may represent may be straight-chain or, when there is a sufficient number (i.e. a minimum of three) of carbon atoms, be branched-chain and/or cyclic. Further, when there is a sufficient number (i.e. a minimum of four) of carbon atoms, such alkyl groups may also be part cyclic/acyclic. Such alkyl groups may also be saturated or, when there is a sufficient number (i.e. a minimum of two) of carbon atoms, be unsaturated.

Halo groups with which $R^2$ and $R^3$ may be substituted include fluoro, chloro, bromo and iodo.

When $R^1$ represents $C(O)OR^3$, preferred $R^3$ groups include:
(a) linear, branched or cyclic $C_{3-6}$ alkyl, for example $C_{4-6}$ cycloalkyl;
(b) $C_{1-2}$ alkylaryl groups, such as benzyl, optionally substituted as indicated hereinbefore.

Preferred compounds of formula Ia include those in which $R^1$ represents $OR^2$.

When $R^1$ represents $OR^2$, preferred $R^2$ groups include:
(a) H;
(b) unsubstituted, linear, branched or cyclic $C_{1-8}$ (e.g. $C_{1-6}$) alkyl, such as linear $C_{1-3}$ alkyl (e.g. ethyl or, particularly, methyl), branched C$_{3-8}$ alkyl (e.g. i-propyl, i-butyl or 4-heptyl) or cyclic C$_{4-7}$ alkyl (i.e. C$_{4-7}$ cycloalkyl, e.g. cyclobutyl or cyclohexyl);

(c) C$_{1-3}$ alkyloxyphenyl (e.g. C$_2$ alkyloxyphenyl), which phenyl group is optionally substituted by one or more substituents as indicated hereinbefore (e.g. trifluoromethyl);

(d) C$_{1-2}$ alkylaryl (e.g. methylaryl), wherein the aryl group is phenyl, pyridinyl, oxazolyl or isoxazolyl, which latter three groups are optionally substituted by one or more substituents as indicated hereinbefore (e.g. methoxy, methyl, bromo and/or chloro).

Preferred compounds of formula Ia include those in which R$^1$ represents OR$^2$ and R$^2$ represents linear, branched (as appropriate), or cyclic (as appropriate), C$_{1-6}$ (e.g. C$_{1-4}$) alkyl, such as methyl, ethyl, n-propyl, i-propyl or cyclobutyl.

Compounds of formula Ia may be prepared by one or more of the following methods:

(a) reaction of a corresponding compound of formula II as hereinbefore defined with a compound of formula XIV,

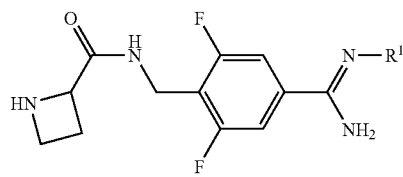

XIV wherein R$^1$ is as hereinbefore defined, for example under similar conditions to those described hereinbefore for synthesis of compounds of formula I;

(b) reaction of a corresponding compound of formula IV as hereinbefore defined with a compound of formula XV,

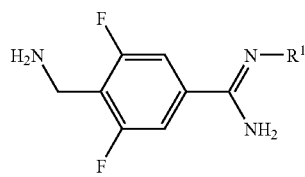

XV wherein R$^1$ is as hereinbefore defined, for example under similar conditions to those described hereinbefore for synthesis of compounds of formula I;

(c) for compounds of formula Ia in which R$^1$ represents OH, reaction of a corresponding compound of formula XVI,

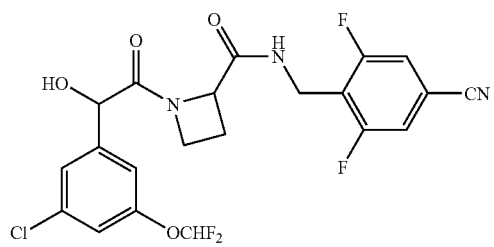

XVI with hydroxylamine, for example under conditions known to those skilled in the art;

(d) for compounds of formula Ia in which R$^1$ represents OR$^2$, reaction of a protected derivative of a corresponding compound of formula I which is, for example, a compound of formula XVII,

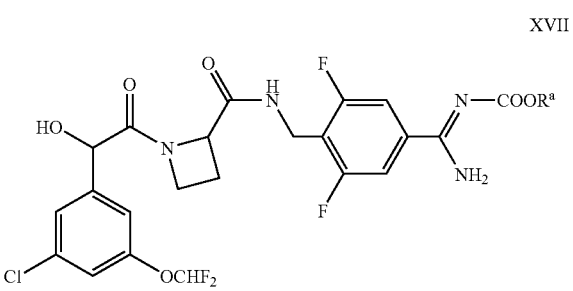

XVII wherein R$^a$ represents, for example, —CH$_2$CH$_2$—Si(CH$_3$)$_3$ or benzyl, or a tautomer thereof, with a compound of formula XVIII,

R$^2$ONH$_2$  XVIII wherein R$^2$ is as hereinbefore defined, or an acid addition salt thereof, for example at between room and reflux temperature in the presence of an appropriate organic solvent (e.g. THF, CH$_3$CN, DMF or DMSO), followed by removal of the —C(O)OR$^a$ group under conditions known to those skilled in the art (e.g. by reacting with QF or TFA (e.g. as described hereinafter));

(e) for compounds of formula Ia in which R$^1$ represents OH, reaction of a compound of formula XVII, as hereinbefore defined, in which R$^a$ represents benzyl with hydroxylamine, or an acid addition salt thereof, for example under conditions that will be well known to those skilled in the art;

(f) for compounds of formula Ia in which R$^1$ represents COOR$^3$, reaction of a corresponding compound of formula I as hereinbefore defined with a compound of formula XIX,

L$^1$COOR$^3$  XIX wherein L$^1$ represents a suitable leaving group, such as halo or nitrophenyl (e.g. 4-nitrophenyl), and R$^3$ is as hereinbefore defined, for example at or around room temperature in the presence of suitable base (e.g. NaOH, for example in aqueous solution) and an appropriate organic solvent (e.g. methylene chloride); or (g) for compounds of formula Ia in which R$^1$ represents OCH$_3$ or OCH$_2$CH$_3$, reaction of a corresponding compound of formula Ia in which R$^1$ represents OH with dimethylsulfate or diethylsulfate, respectively, for example in the presence of a suitable base (e.g. an alkali metal hydroxide such as KOH (for example in aqueous solution at e.g. 50 wt. %)) and an appropriate catalyst (e.g. a quaternary ammonium halide such as benzyltrimethylammonium chloride (for example in CH$_2$Cl$_2$ or THF solution at e.g. 10 wt. %)).

Compounds of formula XVI may be prepared by reaction of a corresponding compound of formula II, as hereinbefore defined, with a compound of formula XX,

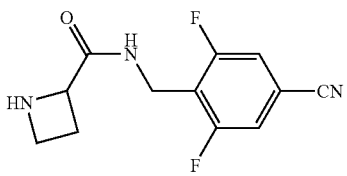

for example under similar conditions to those described hereinbefore for synthesis of compounds of formula I.

Compounds of formulae XVI may alternatively be prepared by reaction of a corresponding compound of formula IV, as hereinbefore defined, with a compound of formula XXI,

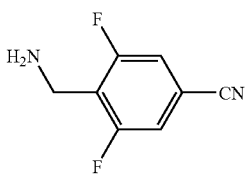

for example under similar conditions to those described hereinbefore for synthesis of compounds of formula I.

Compounds of formula XVII may be prepared by reaction of a corresponding compound of formula II, as hereinbefore defined, with a compound of formula XXII,

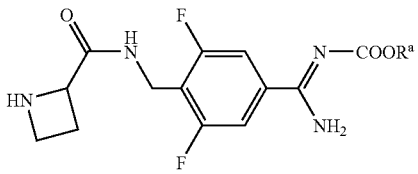

wherein $R^a$ are as hereinbefore defined, for example under similar conditions to those described hereinbefore for synthesis of compounds of formula I.

Alternatively, compounds of formula XVII may be prepared by reaction of a corresponding compound of formula I with a compound corresponding to a compound of formula XIX in which, in place of $R^3$, the group $R^a$ is present, in which $R^a$ is as hereinbefore defined, for example under conditions described above in respect of the preparation of compounds of formula Ia.

Compounds of formulae XIV and XXII may be prepared by reaction of azetidine-2-carboxylic acid with, respectively, a compound of formula XV as hereinbefore defined, or a compound of formula XXIII,

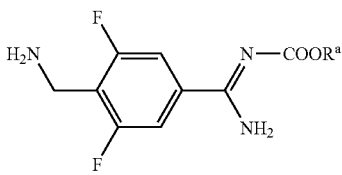

wherein $R^a$ is as hereinbefore defined, for example under similar conditions to those described hereinbefore for synthesis of compounds of formula I.

Compounds of formula XV, XVIII, XIX, XX, XXI and XXIII are either commercially available, are known in the literature, or may be obtained either by analogy with the processes described herein, or by conventional synthetic procedures, in accordance with standard techniques, from readily available starting materials using appropriate reagents and reaction conditions. For example, compounds of formula XX may be prepared by reaction of a corresponding compound of formula XXI with azetidine-2-carboxylic acid, for example under similar conditions to those described hereinbefore.

Compounds of formulae I and Ia, as defined above, and derivatives of either, are referred to hereinafter as "the compounds of the invention".

The compounds of the invention may exhibit tautomerism. All tautomeric forms and mixtures thereof are included within the scope of the invention. Particular tautomeric forms that may be mentioned include those connected with the position of the double bond in the amidine functionality in a compound of formula Ia, and the position of the substituent $R^1$.

Compounds of the invention also contain two or more asymmetric carbon atoms and may therefore exhibit optical and/or diastereoisomerism. Diastereoisomers may be separated using conventional techniques, e.g. chromatography. The various stereoisomers may be isolated by separation of a racemic or other mixture of the compounds using conventional, e.g. HPLC techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Compounds of the invention in which the

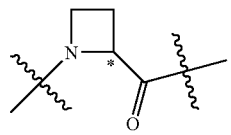

fragment is in the S-configuration are preferred.

Preferred compounds of the invention also include those in which the structural fragment

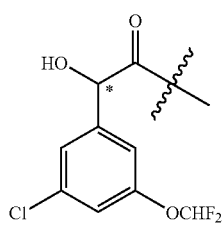

is in the R-configuration.

The wavy lines on the bonds in the above two fragments signify the bond positions of the fragments.

Thus, preferred compounds of the invention include:
Ph(3-Cl)(5-OCHF$_2$)—(R)CH(OH)C(O)—(S)Aze-Pab(2,6-diF);
Ph(3-Cl)(5-OCHF$_2$)—(R)CH(OH)C(O)—(S)Aze-Pab(2,6-diF)(OMe); and
Ph(3-Cl)(5-OCHF$_2$)—(R)CH(OH)C(O)—(S)Aze-Pab(2,6-diF)(OH).

It will be appreciated by those skilled in the art that in the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters.

Suitable protecting groups for amino and amidino include t-butyloxycarbonyl, benzyloxycarbonyl or 2-trimethylsilylethoxycarbonyl (Teoc). Amidino nitrogens may also be protected by hydroxy or alkoxy groups, and may be either mono- or diprotected.

The protection and deprotection of functional groups may take place before or after coupling, or before or after any other reaction in the above-mentioned schemes.

Protecting groups may be removed in accordance with techniques that are well known to those skilled in the art and as described hereinafter.

Persons skilled in the art will appreciate that, in order to obtain compounds of the invention in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", 3$^{rd}$ edition, T. W. Greene & P. G. M. Wutz, Wiley-Interscience (1999).

Protected derivatives of compounds of the invention may be converted chemically to compounds of the invention using standard deprotection techniques (e.g. hydrogenation). The skilled person will also appreciate that certain compounds of formula Ia may also be referred to as being "protected derivatives" of compounds of formula I.

Medical and Pharmaceutical Use

Compounds of the invention may possess pharmacological activity as such. Compounds of the invention that may possess such activity include, but are not limited to, compounds of formula I.

However, other compounds of the invention (including compounds of formula Ia) may not possess such activity, but may be administered parenterally or orally, and may thereafter be metabolised in the body to form compounds that are pharmacologically active (including, but not limited to, corresponding compounds of formula I). Such compounds (which also includes compounds that may possess some pharmacological activity, but that activity is appreciably lower than that of the "active" compounds to which they are metabolised), may therefore be described as "prodrugs" of the active compounds.

Thus, the compounds of the invention are useful because they possess pharmacological activity, and/or are metabolised in the body following oral or parenteral administration to form compounds which possess pharmacological activity. The compounds of the invention are therefore indicated as pharmaceuticals.

According to a further aspect of the invention there is thus provided the compounds of the invention for use as pharmaceuticals.

In particular, compounds of the invention are potent inhibitors of thrombin either as such and/or (e.g. in the case of prodrugs), are metabolised following administration to form potent inhibitors of thrombin, for example as may be demonstrated in the tests described below.

By "prodrug of a thrombin inhibitor", we include compounds that form a thrombin inhibitor, in an experimentally-detectable amount, and within a predetermined time (e.g. about 1 hour), following oral or parenteral administration (see, for example, Test E below) or, alternatively, following incubation in the presence of liver microsomes (see, for example, Test G below).

The compounds of the invention are thus expected to be useful in those conditions where inhibition of thrombin is required, and/or conditions where anticoagulant therapy is indicated, including the following:

The treatment and/or prophylaxis of thrombosis and hypercoagulability in blood and/or tissues of animals including man. It is known that hypercoagulability may lead to thrombo-embolic diseases. Conditions associated with hypercoagulability and thrombo-embolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis, as well as coagulation syndromes (e.g. disseminated intravascular coagulation (DIC)) and vascular injury in general (e.g. due to surgery).

The treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis (e.g. DVT) and pulmonary embolism, arterial thrombosis (e.g. in myocardial infarction, unstable angina, thrombosis-based stroke and peripheral arterial thrombosis), and systemic embolism usually from the atrium during atrial fibrillation (e.g. non-valvular atrial fibrillation) or from the left ventricle after transmural myocardial infarction, or caused by congestive heart failure; prophylaxis of re-occlusion (i.e. thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease and the formation of atherosclerotic plaques, cerebral arterial disease, cerebral infarction, cerebral thrombosis, cerebral embolism, peripheral arterial disease, ischaemia, angina (including unstable angina), reperfilsion damage, restenosis after percutaneous trans-luminal angioplasty (PTA) and coronary artery bypass surgery.

Compounds of the invention that inhibit trypsin and/or thrombin may also be useful in the treatment of pancreatitis.

The compounds of the invention are thus indicated both in the therapeutic and/or prophylactic treatment of these conditions.

According to a further aspect of the present invention, there is provided a method of treatment of a condition where inhibition of thrombin is required which method comprises administration of a therapeutically effective amount of a compound of the invention to a person suffering from, or susceptible to, such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising compound of the invention in a pharmaceutically acceptable dosage form.

Depending upon the disorder and patient to be treated and the route of administration, the compositions may be administered at varying doses.

The compounds of the invention may also be combined and/or co-administered with any antithrombotic agent(s) with a different mechanism of action, such as one or more of the following: the antiplatelet agents acetylsalicylic acid, ticlopidine and clopidogrel; thromboxane receptor and/or synthetase inhibitors; fibrinogen receptor antagonists; prostacyclin mimetics; phosphodiesterase inhibitors; ADP-receptor ($P_2T$) antagonists; and inhibitors of carboxypeptidase U (CPU).

The compounds of the invention may further be combined and/or co-administered with thrombolytics such as one or more of tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is provided a pharmaceutical formulation including a compound of the invention, in admixture with a pharmaceutically acceptable adjuvant, diluent or carrier.

Suitable daily doses of the compounds of the invention in therapeutic treatment of humans are about 0.001–100 mg/kg body weight at peroral administration and 0.001–50 mg/kg body weight at parenteral administration, excluding the weight of any acid counter-ion.

For the avoidance of doubt, as used herein, the term "treatment" includes therapeutic and/or prophylactic treatment.

Compounds of the invention have the advantage that they may be more efficacious, be less toxic, be longer acting, have a broader range of activity, be more potent, produce fewer side effects, be more easily absorbed, and/or have a better pharmacokinetic profile (e.g. higher oral bioavailability and/or lower clearance), than, and/or have other useful pharmacological, physical, or chemical, properties over, compounds known in the prior art.

Compounds of the invention may have the further advantage that they may be administered less frequently than compounds known in the prior art.

Biological Tests

The following test procedures may be employed.

Test A

Determination of Thrombin Clotting Time (TT)

The inhibitor solution (25 μL) is incubated with plasma (25 μL) for three minutes. Human thrombin (T 6769; Sigma Chem. Co or Hematologic Technologies) in buffer solution, pH 7.4 (25 μL, 4.0 NIH units/mL), is then added and the clotting time measured in an automatic device (KC 10; Amelung).

The thrombin clotting time (TT) is expressed as absolute values (seconds) as well as the ratio of TT without inhibitor ($TT_0$) to TT with inhibitor ($TT_i$). The latter ratios (range 1–0) are plotted against the concentration of inhibitor (log transformed) and fitted to sigmoidal dose-response curves according to the equation $$y=a/[1+(x/IC_{50})^s]$$

where: a=maximum range, i.e. 1; s=slope of the dose-response curve; and $IC_{50}$=the concentration of inhibitor that doubles the clotting time. The calculations are processed on a PC using the software program GraFit Version 3, setting equation equal to: Start at 0, define end=1 (Erithacus Software, Robin Leatherbarrow,.Imperial College of Science, London, UK).

Test B

Determination of Thrombin Inhibition with a Chromogenic, Robotic Assay

The thrombin inhibitor potency is measured with a chromogenic substrate method, in a Plato 3300 robotic microplate processor (Rosys AG, CH-8634 Hombrechtikon, Switzerland), using 96-well, half volume microtiter plates Costar, Cambridge, Mass., USA; Cat No 3690). Stock solutions of test substance in DMSO (72 μL), 0.1–1 mmol/L, are diluted serially 1:3 (24+48 μL) with DMSO to obtain ten different concentrations, which are analysed as samples in the assay. 2 μL of test sample is diluted with 124 μL assay buffer, 12 μL of chromogenic substrate solution (S-2366, Chromogenix, Mölndal, Sweden) in assay buffer and finally 12 μL of α-thrombin solution (Human α-thrombin, Sigma Chemical Co. or Hematologic Technologies) in assay buffer, are added, and the samples mixed. The final assay concentrations are: test substance 0.00068–13.3 μmol/L, S-2366 0.30 mmol/L, α-thrombin 0.020 NIHU/mL. The linear absorbance increment during 40 minutes incubation at 37° C. is used for calculation of percentage inhibition for the test samples, as compared to blanks without inhibitor. The $IC_{50}$-robotic value, corresponding to the inhibitor concentration which causes 50% inhibition of the thrombin activity, is calculated from a log concentration vs. % inhibition curve.

Test C

Determination of the Inhibition Constant $K_i$ for Human Thrombin $K_i$-determinations are made using a chromogenic substrate method, performed at 37° C. on a Cobas Bio centrifugal analyser (Roche, Basel, Switzerland). Residual enzyme activity after incubation of human α-thrombin with various concentrations of test compound is determined at three different substrate concentrations, and is measured as the change in optical absorbance at 405 nm.

Test compound solutions (100 μL; normally in buffer or saline containing BSA 10 g/L) are mixed with 200 μL of human α-thrombin (Sigma Chemical Co) in assay buffer (0.05 mol/L Tris-HCl pH 7.4, ionic strength 0.15 adjusted with NaCl) containing BSA (10 g/L), and analysed as samples in the Cobas Bio. A 60 μL sample, together with 20 μL of water, is added to 320 μL of the substrate S-2238 (Chromogenix AB, Mölndal, Sweden) in assay buffer, and the absorbance change (ΔA/min) is monitored. The final concentrations of S-2238 are 16, 24 and 50 μmol/L and of thrombin 0.125 NIH U/mL.

The steady state reaction rate is used to construct Dixon plots, i.e. diagrams of inhibitor concentration vs. 1/(ΔA/min). For reversible, competitive inhibitors, the data points for the different substrate concentrations typically form straight lines which intercept at $x=-K_i$.

Test D

Determination of Activated Partial Thromboplastin Time (APTT)

APTT is determined in pooled normal human citrated plasma with the reagent PTT Automated 5 manufactured by Stago. The inhibitors are added to the plasma (10 μL inhibitor solution to 90 μL plasma) and incubated with the APTT reagent for 3 minutes followed by the addition of 100 μL of calcium chloride solution (0.025 M) and APTT is determined by use of the coagulation analyser KC10 (Amelung) according to the instructions of the reagent producer.

The clotting time is expressed as absolute values (seconds) as well as the ratio of APTT without inhibitor ($APTT_0$) to APTT with inhibitor ($APTT_i$). The latter ratios (range 1–0) are plotted against the concentration of inhibitor (log transformed) and fitted to sigmoidal dose-response curves according to the equation $$y=a/[1+(x/IC_{50})^s]$$

where: a=maximum range, i.e. 1; s=slope of the dose-response curve; and $IC_{50}$=the concentration of inhibitor that doubles the clotting time. The calculations are processed on a PC using the software program GraFit Version 3, setting equation equal to: Start at 0, define end=1 (Erithacus Software, Robin Leatherbarrow, Imperial College of Science, London, UK). $IC_{50}APTT$ is defined as the concentration of inhibitor in human plasma that doubles the Activated Partial Thromboplastin Time.

Test E

Determination of Thrombin Time ex vivo

The inhibition of thrombin after oral or parenteral administration of the compounds of the invention, dissolved in ethanol:SolutolK:water (5:5:90), is examined in conscious rats which, one or two days prior to the experiment, are equipped with a catheter for blood sampling from the carotid artery. On the experimental day blood samples are withdrawn at fixed times after the administration of the compound into plastic tubes containing 1 part sodium citrate solution (0.13 mol per L) and 9 parts of blood. The tubes are centrifuged to obtain platelet poor plasma.

50 μL of plasma samples are precipitated with 100 μL of cold acetonitrile. The samples are centrifuged for 10 minutes at 4000 rpm. 75 μL of the supernatant is diluted with 75 μL of 0.2% formic acid. 10 μL volumes of the resulting solutions are analysed by LC-MS/MS and the concentrations of thrombin inhibitor are determined using standard curves.

Test F

Determination of Plasma Clearance in Rat

Plasma clearance is estimated in male Sprague Dawley rats. The compound is dissolved in water and administered as a subcutaneous bolus injection at a dose of 4 μmol/kg. Blood samples are collected at frequent intervals up to 5 hours after drug administration. Blood samples are centrifuged and plasma is separated from the blood cells and transferred to vials containing citrate (10% final concentration). 50 μL of plasma samples are precipitated with 100 μL of cold acetonitrile. The samples are centrifuged for 10 minutes at 4000 rpm. 75 μL of the supernatant is diluted with 75 μL of 0.2% formic acid. 10 μL volumes of the resulting solutions are analysed by LC-MS/MS and the concentrations of thrombin inhibitor are determined using standard curves. The area under the plasma concentration-time profile is estimated using the log/linear trapezoidal rule and extrapolated to infinite time. Plasma clearance (CL) of the compound is then determined as $$CL=Dose/AUC$$

The values are reported in mL/min/kg.

Test G

Determination of in vitro Stability

Liver microsomes are prepared from Sprague-Dawley rats and human liver samples according to internal SOPs. The compounds are incubated at 37° C. at a total microsome protein concentration of 3 mg/mL in a 0.05 mol/L TRIS buffer at pH 7.4, in the presence of the cofactors NADH (2.5 mmol/L) and NADPH (0.8 mmol/L). The initial concentration of compound is 5 or 10 μmol/L. Samples are taken for analysis up to 60 minutes after the start of the incubation. The enzymatic activity in the collected sample is immediately stopped by adding 20% myristic acid at a volume corresponding to 3.3% of the total sample volume. The concentration of compound remaining (FINAL CONC) in the 60 min. sample is determined by means of LCMS using a sample collected at zero time as reference (START CONC). The % of degraded thrombin inhibitor is calculated as:

$$100\% \times \frac{[START\,CONC] - [FINAL\,CONC]}{[START\,CONC]}$$

Test H

Arterial Thrombosis Model

Vessel damage is induced by applying ferric chloride ($FeCl_3$) topically to the carotid artery. Rats are anaesthetised with an intraperitoneal injection of sodium pentobarbital (80 mg/kg; Apoteksbolaget; Umeå, Sweden), followed by continuous infusion (12 mg/kg/h) throughout the experiment. Rat body temperature is maintained at 38° C. throughout the experiment by external heating. The experiment starts with a 5 minutes control period. Five minutes later, human $^{125}$I-fibrinogen (80 kBq; IM53; Amersham International, Buckinghamshire, UK) is given intravenously and is used as a marker for the subsequent incorporation of fibrin(ogen) into the thrombus. The proximal end of the carotid artery segment is placed in a plastic tube (6 mm; Silastic®; Dow Corning, Mich., USA) opened lengthways, containing FeCl$_3$-soaked (2 μL; 55% w/w; Merck, Darmstadt, Germany) filter paper (diameter 3 mm; 1F; Munktell, Grycksbo, Sweden). The left carotid artery is exposed to FeCl$_3$ for 10 minutes and is then removed from the plastic tube and soaked in saline. Fifty minutes later, the carotid artery is removed and rinsed in saline. Reference blood samples are also taken for determination of blood $^{125}$I-activity, 10 minutes after the injection of $^{125}$I-fibrinogen, and at the end of the experiment. The $^{125}$I-activity in the reference blood samples and the vessel segment are measured in a gamma counter (1282 Compugamma; LKB Wallac Oy, Turku, Finland) on the same day as the experiment is performed. The thrombus size is determined as the amount of $^{125}$I-activity incorporated in the vessel segment in relation to the $^{125}$I-activity in the blood (cpm/mg).

General Experimental Details

TLC was performed on silica gel. Chiral HPLC analysis was performed using a 46 mm×250 mm Chiralcel OD column with a 5 cm guard column.

The column temperature was maintained at 35° C. A flow rate of 1.0 mL/min was used. A Gilson 115 UV detector at 228 nm was used. The mobile phase consisted of hexanes, ethanol and trifluroacetic acid and the appropriate ratios are listed for each compound. Typically, the product was dissolved in a minimal amount of ethanol and this was diluted with the mobile phase.

LC-MS/MS was performed using a HP-1100 instrument equipped with a CTC-PAL injector and a 5 μm, 4×100 mm ThermoQuest, Hypersil BDS-C18 column. An API-3000 (Sciex) MS detector was used. The flow rate was 1.2 mL/min and the mobile phase (gradient) consisted of 10–90% acetonitrile with 90–10% of 4 mM aq. ammonium acetate, both containing 0.2% formic acid.

$^1$H NMR spectra were recorded using tetramethylsilane as the internal standard. $^{13}$C NMR spectra were recorded using the listed deuterated solvents as the internal standard.

EXAMPLE 1

Ph(3-Cl)(5-OCHF$_2$)—(R)CH(OH)C(O)—(S)Aze-Pab(2,6-diF)

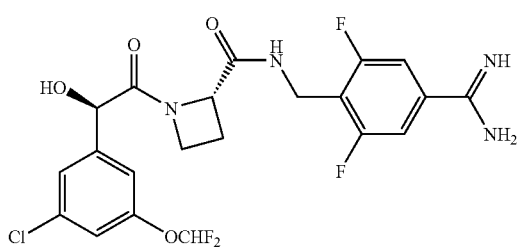

(i) 3-Chloro-5-methoxybenzaldehyde 3,5-Dichloroanisole (74.0 g, 419 mmol) in THF (200 mL) was added dropwise to magnesium metal (14.2 g, 585 mmol, pre-washed with 0.5 N HCl) in THF (100 mL) at 25° C. After the addition, 1,2-dibromoethane (3.9 g, 20.8 mmol) was added dropwise. The resultant dark brown mixture was heated at reflux for 3 h. The mixture was cooled to 0° C., and N,N-dimethylformamide (60 mL) was added in one portion. The mixture was partitioned with diethyl ether (3×400 mL) and 6N HCl (500 mL). The combined organic extracts were washed with brine (300 mL), dried (Na$_2$SO$_4$), filtered and concentrated in vacuo to give an oil. Flash chromatography (2×) on silica get eluting with Hex:EtOAc (4:1) afforded the sub-title compound (38.9 g, 54%) as a yellow oil.

$^1$H NMR (300 MHz, CDCl$_3$) δ 9.90 (s, 1H), 7.53 (s, 1H), 7.38 (s, 1H), 7.15 (s, 1H), 3.87 (s, 3H).

(ii) 3-Chloro-5-hydroxybenzaldehyde

A solution of 3-chloro-5-methoxybenzaldehyde (22.8 g, 134 mmol; see step (i) above) in CH$_2$Cl$_2$ (250 mL) was cooled to 0° C. Boron tribromide (15.8 mL, 167 mmol) was added dropwise over 15 min. After stirring, the reaction mixture for 2 h, H$_2$O (50 mL) was added slowly. The solution was then extracted with Et$_2$O (2×100 mL). The organic layers were combined, dried (Na$_2$SO$_4$), filtered and concentrated in vacuo. Flash chromatography on silica gel eluting with Hex:EtOAc (4:1) afforded the sub-title compound (5.2 g, 25%).

$^1$H NMR (300 MHz, CDCl$_3$) δ 9.85 (s, 1H), 7.35 (s, 1H), 7.20 (s, 1H), 7.10 (s, 1H), 3.68 (s, 1H)

(iii) 3-Chloro-5-difluoromethoxybenzaldehyde

A solution of 3-chloro-5-hydroxybenzaldehyde (7.5 g, 48 mmol; see step (ii) above) in 2-propanol (250 mL) and 30% KOH (100 mL) was heated to reflux. While stirring, CHClF$_2$ was bubbled into the reaction mixture for 2 h. The reaction mixture was cooled, acidified with 1N HCl and extracted with EtOAc (2×100 mL). The organics were washed with brine (100 mL), dried (Na$_2$SO$_4$), filtered and concentrated in vacuo. Flash chromatography on silica gel eluting with Hex:EtOAc (4:1) afforded the sub-title compound (4.6 g, 46%).

$^1$H NMR (300 MHz, CDCl$_3$) δ 9.95 (s, 1H), 7.72 (s, 1H), 7.52 (s, 1H), 7.40 (s, 1H), 6.60 (t, J$_{H-F}$=71.1 Hz, 1H)

(iv) Ph(3-Cl)(5-OCHF$_2$)-(R,S)CH(OTMS)CN

A solution of 3-chloro-5-difluoromethoxybenzaldehyde (4.6 g, 22.3 mmol; see step (iii) above) in CH$_2$Cl$_2$ (200 mL) was cooled to 0° C. ZnI$_2$ (1.8 g, 5.6 mmol) and trimethylsilyl cyanide (2.8 g, 27.9 mmol) were added and the reaction mixture was allowed to warm to room temperature and stirred for 15 h. The mixture was partially concentrated in vacuo yielding the sub-title compound as a liquid, which was used directly in step (v) below without further purification or characterization.

(v) Ph(3-Cl)(5-OCHF$_2$)-(R,S)CH(OH)CH)OEt

Ph(3-Cl)(5-OCHF$_2$)-(R,S)CH(OTMS)CN (6.82 g, assume 22.3 mmol; see step (iv) above) was added dropwise to HCl/EtOH (500 mL). The reaction mixture was stirred 15 h, then partially concentrated in vacuo yielding the sub-title compound as a liquid, which was used in step (vi) without further purification or characterization.

(vi) Ph(3-Cl)(5-OCHF$_2$)-(R,S)CH(OH)C(O)OEt

Ph(3-Cl)(5-OCHF$_2$)-(R,S)CH(OH)C(NH)OEt (6.24 g, assume 22.3 mmol; see step (v) above) was dissolved in THF (250 mL), 0.5M H$_2$SO$_4$ (400 mL) was added and the reaction was stirred at 40° C. for 65 h, cooled and then partially concentrated in vacuo to remove most of the THF. The reaction mixture was then extracted with Et$_2$O (3×100 mL), dried (Na$_2$SO$_4$), filtered and concentrated in vacuo to afford the sub-title compound as a solid, which was used in step (vii) without further purification or characterization.

(vii) Ph(3-Cl)(5-OCHF$_2$)-(R,S)CH(OH)C(O)OH

A solution of Ph(3-Cl)(5-OCHF$_2$)-(R,S)CH(OH)C(O)OEt (6.25 g, assume 22.3 mmol; see step (vi) above) in 2-propanol (175 mL) and 20% KOH (350 mL) was stirred at room temperature 15 h. The reaction was then partially concentrated in vacuo to remove most of the 2-propanol. The remaining mixture was acidified with 1M H$_2$SO$_4$, extracted with Et$_2$O (3×100 mL), dried (Na$_2$SO$_4$) and concentrated in vacuo to give a solid. Flash chromatography on silica gel eluting with CHCl$_3$:MeOH:concentrated NH$_4$OH (6:3:1) afforded the ammonium salt of the sub-title compound. The ammonium salt was then dissolved in a mixture of EtOAc (75 mL) and H$_2$O (75 mL) and acidified with 2N HCl. The organic layer was separated and washed with brine (50 mL), dried (Na$_2$SO$_4$) and concentrated in vacuo to afford the sub-title compound (3.2 g, 57% from steps (iv) to (vii)).

$^1$H NMR (300 MHz, CD$_3$OD) δ 7.38 (s, 1H), 7.22 (s, 1H), 7.15 (s, 1H), 6.89 (t, J$_{H-F}$=71.1 Hz, 1H), 5.16 (s, 1H)

(viii) Ph(3-Cl)(5-OCHF$_2$)—(R)CH(OH)C(O)OH (a) and Ph(3-Cl)(5-OCHF$_2$)—(S)CH(OAc)C(O)OH (b)

A mixture of Ph(3-Cl)(5-OCHF$_2$)-(R,S)CH(OH)C(O)OH (3.2 g, 12.7 mmol; see step (vii) above) and Lipase PS "Amano" (~2.0 g) in vinyl acetate (125 mL) and MTBE (125 mL) was heated at reflux for 48 h. The reaction mixture was cooled, filtered through Celite® and the filter cake washed with EtOAc. The filtrate was concentrated in vacuo and subjected to flash chromatography on silica gel eluting with CHCl$_3$:MeOH:concentrated NH$_4$OH (6:3:1) yielding the ammonium salts of the sub-title compounds (a) and (b). Compound (a) as a salt was dissolved in H$_2$O, acidified with 2N HCl and extracted with EtOAc. The organic layer was washed with brine, dried (Na$_2$SO$_4$), filtered and concentrated in vacuo to afford the sub-title compound (a) (1.2 g, 37%).

For sub-title compound (a)
$^1$H NMR (300 MHz, CD$_3$OD) δ 7.38 (s, 1H), 7.22 (s, 1H), 7.15 (s, 1H), 6.89 (t, J$_{H-F}$=71.1 Hz, 1H), 5.17 (s, 1H)

(ix) 2,6-Difluoro-4[(methylsulfinyl)(methylthio)methyl]benzonitrile (Methylsulfinyl)(methylthio)methane (7.26 g, 0.0584 mol) was dissolved in 100 mL of dry THF under argon and was cooled to −78° C. Butyllithium in hexane (16 mL 1.6M, 0.0256 mol) was added dropwise with stirring. The mixture was stirred for 15 min. Meanwhile, a solution of 3,4,5-trifluorobenzonitrile (4.0 g, 0.025 mmol) in 100 mL of dry THF was cooled to −78° C. under argon and the former solution was added through a cannula to the latter solution over a period of 35 min. After 30 min, the cooling bath was removed and when the reaction had reached room temperature it was poured into 400 mL of water. The THF was evaporated and the remaining aqueous layer was extracted three times with diethyl ether. The combined ether phase was washed with water, dried (Na$_2$SO$_4$) and evaporated. Yield: 2.0 g (30%).

$^1$H NMR (500 MHz, CDCl$_3$) δ 7.4–7.25 (m, 2H), 5.01 (s, 1H, diasteromer), 4.91 (s, 1H, diasteromer), 2.88 (s, 3H, diasteromer), 2.52 (s, 3H, diasteromer), 2.49 (s, 3H, diasteromer), 2.34 (s, 3H, diasteromer), 1.72 (broad, 1H)

(x) 2,6-Difluoro-4-formylbenzonitrile 2,6-Difluoro-4[(methylsulfinyl)(methylthio)methyl]benzonitrile (2.17 g, 8.32 mmol; see step (ix) above) was dissolved in 90 mL of THF and 3.5 mL of concentrated sulfuric acid was added. The mixture was left at room temperature for 3 days and subsequently poured into 450 mL of water. Extraction three times with EtOAc followed and the combined ethereal phase was washed twice with aqueous sodium bicarbonate and with brine, dried (Na$_2$SO$_4$) and evaporated. Yield: 1.36 g (98%). The position of the formyl group was established by $^{13}$C NMR. The signal from the fluorinated carbons at 162.7 ppm exhibited the expected coupling pattern with two coupling constants in the order of 260 Hz and 6.3 Hz respectively corresponding to an ipso and a meta coupling from the fluorine atoms.

$^1$H NMR (400 MHz, CDCl$_3$) δ 10.35 (s, 1H), 7.33 (m, 2H)

(xi) 2,6-Difluoro-4-hydroxymethylbenzonitrile 2,6-Difluoro-4-formylbenzonitrile (1.36 g, 8.13 mmol; see step (x) above) was dissolved in 25 mL of methanol and cooled on an ice bath. Sodium borohydride (0.307 g, 8.12 mmol) was added in portions with stirring and the reaction was left for 65 min. The solvent was evaporated and the residue was partitioned between diethyl ether and aqueous sodium bicarbonate. The ethereal layer was washed with more aqueous sodium bicarbonate and brine, dried (Na$_2$SO$_4$) and evaporated. The crude product crystallised soon and could be used without further purification. Yield: 1.24 g (90%).

$^1$H NMR (400 MHz, CDCl$_3$) δ 7.24 (m, 2H), 4.81 (s, 2H), 2.10 (broad, 1H)

(xii) 4-Cyano-2,6-difluorobenzyl methanesulfonate

To an ice cooled solution of 2,6-difluoro-4-hydroxymethylbenzonitrile (1.24 g, 7.32 mmol; see step (xi) above) and methanesulfonyl chloride (0.93 g, 8.1 mmol) in 60 mL of methylene chloride was added triethylamine (0.81 g, 8.1 mmol) with stirring. After 3 h at 0° C., the mixture was washed twice with 1M HCl and once with water, dried (Na$_2$SO$_4$) and evaporated. The product could be used without further purification. Yield: 1.61 g (89%).

$^1$H NMR (300 MHz, CDCl$_3$) δ 7.29 (m, 2H), 5.33 (s, 2H), 3.07 (s, 3H)

(xiii) 4-Azidomethyl-2,6-difluorobenzonitrile

A mixture of 4-cyano-2,6-difluorobenzyl methanesulfonate (1.61 g, 6.51 mmol; see step (xii) above) and sodium azide (0.72 g, 0.0111 mol) in 10 mL of water and 20 mL of DMF was stirred at room temperature overnight. The resultant was subsequently poured into 200 mL of water and extracted three times with diethyl ether. The combined ethereal phase was washed five times with water, dried (Na$_2$SO$_4$) and evaporated. A small sample was evaporated for NMR purposes and the product crystallised. The rest was evaporated cautiously but not until complete dryness. Yield (theoretically 1.26 g) was assumed to be almost quantitative based on NMR and analytical HPLC.

$^1$H NMR (400 MHz, CDCl$_3$) δ 7.29 (m, 2H), 4.46 (s, 2H)

(xiv) 4-Aminomethyl-2,6-difluorobenzonitrile

This reaction was carried out according to the procedure described in *J. Chem. Res.* (*M*) (1992) 3128. To a suspension of 520 mg of 10% Pd/C (50% moisture) in 20 mL of water was added a solution of sodium borohydride (0.834 g, 0.0221 mol) in 20 mL of water. Some gas evolution resulted. 4-Azidomethyl-2,6-difluorobenzonitrile (1.26 g, 6.49 mmol; see step (xiii) above) was dissolved in 50 mL of THF and added to the aqueous mixture on an ice bath over 15 min. The mixture was stirred for 4 h, whereafter 20 mL of 2M HCl was added and the mixture was filtered through Celite. The Celite was rinsed with more water and the combined aqueous phase was washed with EtOAc and subsequently made alkaline with 2M NaOH. Extraction three times with methylene chloride followed and the combined organic phase was washed with water, dried (Na$_2$SO$_4$) and evaporated. Yield: 0.87 g (80%).

$^1$H NMR (400 MHz, CDCl$_3$) δ 7.20 (m, 2H), 3.96 (s, 2H), 1.51 (broad, 2H)

(xv) 2,6-Difluoro-4-tert-butoxycarbonylaminomethylbenzonitrile

A solution of 4-aminomethyl-2,6-difluorobenzonitrile (0.876 g, 5.21 mmol; see step (xiv) above) was dissolved in 50 mL of THF and di-tert-butyl dicarbonate (1.14 g, 5.22 mmol) in 10 mL of THF was added. The mixture was stirred for 3.5 h. The THF was evaporated and the residue was partitioned between water and EtOAc. The organic layer was washed three times with 0.5 M HCl and water, dried (Na$_2$SO$_4$) and evaporated. The product could be used without further purification. Yield: 1.38 g (99%).

$^1$H NMR (300 MHz, CDCl$_3$) δ 7.21 (m, 2H), 4.95 (broad, 1H), 4.43 (broad, 2H), 1.52 (s, 9H)

(xvi) Boc-Pab(2,6-diF)(OH)

A mixture of 2,6-difluoro-4-tert-butoxycarbonylaminomethylbenzonitrile (1.38 g, 5.16 mmol; see step (xv) above), hydroxylamine hydrochloride (1.08 g, 0.0155 mol) and triethylamine (1.57 g, 0.0155 mol) in 20 mL of ethanol was stirred at room temperature for 36 h. The solvent was evaporated and the residue was partitioned between water and methylene chloride. The organic layer was washed with water, dried (Na$_2$SO$_4$) and evaporated. The product could be used without further purification. Yield: 1.43 g (92%).

$^1$H NMR (500 MHz, CD$_3$OD) δ 7.14 (m, 2H), 4.97 (broad, 1H), 4.84 (broad, 2H), 4.40 (broad, 2H), 1.43 (s, 9H)

(xvii) Boc-Pab(2,6-diF)×HOAc

This reaction was carried out according to the procedure described by Judkins et al, *Synth. Comm.* (1998) 4351. Boc-Pab(2,6-diF)(OH) (1.32 g, 4.37 mmol; see step (xvi) above), acetic anhydride (0.477 g, 4.68 mmol) and 442 mg of 10% Pd/C (50% moisture) in 100 mL of acetic acid was hydrogenated at 5 atm pressure for 3.5 h. The mixture was filtered through Celite, rinsed with ethanol and evaporated. The residue was freeze-dried from acetonitrile and water and a few drops of ethanol. The sub-title product could be used without further purification. Yield: 0.1.49 g (99%).

$^1$H NMR (400 MHz, CD$_3$OD) δ 7.45 (m, 2H), 4.34 (s, 2H), 1.90 (s, 3H), 1.40 (s, 9H)

(xviii) Boc-Pab(2,6-diF)(Teoc)

To a solution of Boc-Pab(2,6-diF)×HOAc (1.56 g, 5.49 mmol; see step (xvii) above) in 100 mL of THF and 1 mL of water was added 2-(trimethylsilyl)ethyl p-nitrophenyl carbonate (1.67 g, 5.89 mmol). A solution of potassium carbonate (1.57 g, 0.0114 mol) in 20 mL of water was added dropwise over 5 min. The mixture was stirred overnight. The THF was evaporated and the residue was partitioned between water and methylene chloride. The aqueous layer was extracted with methylene chloride and the combined organic phase was washed twice with aqueous sodium bicarbonate, dried (Na$_2$SO$_4$) and evaporated. Flash chromatography on silica gel with heptane/EtOAc=2/1 gave 1.71 g (73%) of pure compound.

$^1$H NMR (400 MHz, CDCl$_3$) δ 7.43 (m, 2H), 4.97 (broad, 1H), 4.41 (broad, 2H), 4.24 (m, 2H), 1.41 (s, 9H), 1.11 (m, 2H), 0.06 (s, 9H)

(xix) Boc-(S)Aze-Pab(2,6-diF)(Teoc)

Boc-Pab(2,6-diF)(Teoc) (1.009 g, 2.35 mmol; see step (xviii) above) was dissolved in 50 mL of EtOAc saturated with HCl(g). The mixture was left for 10 min., evaporated and dissolved in 18 mL of DMF, and then cooled on an ice bath. Boc-(S)Aze-OH (0.450 g, 2.24 mmol), PyBOP (1.24 g, 2.35 mmol) and lastly diisopropylethyl amine (1.158 g, 8.96 mmol) were added. The reaction mixture was stirred for 2 h and then poured into 350 mL of water and extracted three times with EtOAc. The combined organic phase was washed with brine, dried (Na$_2$SO$_4$) and evaporated. Flash chromatography on silica gel with heptane:EtOAc (1:3) gave 1.097 g (96%) of the desired compound.

$^1$H NMR (500 MHz, CDCl$_3$) δ 7.46 (m, 2H), 4.65–4.5 (m, 3H), 4.23 (m, 2H), 3.87 (m, 1H), 3.74 (m, 1H), 2.45–2.3 (m, 2H), 1.40 (s, 9H), 1.10 (m, 2H), 0.05 (s, 9H)

(xx) Ph(3-Cl)(5-OCHF$_2$)—(R)CH(OH)C(O)—(S)Aze-Pab(2,6-diF)(Teoc)

Boc-(S)Aze-Pab(2,6-diF)(Teoc) (0.256 g, 0.500 mmol; see step (xix) above) was dissolved in 20 mL of EtOAc saturated with HCl(g). The mixture was left for 10 min. and evaporated and dissolved in 5 mL of DMF. Ph(3-Cl)(5-OCHF$_2$)—(R)CH(OH)C(O)OH (0.120 g, 0.475 mmol; see step (viii) above), PyBOP (0.263 g, 0.498 mmol) and lastly diisopropylethyl amine (0.245 g, 1.89 mmol were added. The reaction mixture was stirred for 2 h and then poured into 350 mL of water and extracted three times with EtOAc. The combined organic phase was washed with brine, dried (Na$_2$SO$_4$) and evaporated. Flash chromatography on silica gel with EtOAc gave 0.184 g (60%) of the desired sub-title compound.

$^1$H NMR (400 MHz, CD$_3$OD, mixture of rotamers) δ 7.55–7.45 (m, 2H), 7.32 (m, 1H, major rotamer), 7.27 (m, 1H, minor rotamer), 7.2–7.1 (m, 2H), 6.90 (t, 1H, major rotamer), 6.86 (t, 1H, minor rotamer), 5.15 (s, 1H, major rotamer), 5.12 (m, 1H, minor rotamer), 5.06 (s, 1H, minor rotamer), 4.72 (m, 1H, major rotamer), 4.6–4.45 (m, 2H), 4.30 (m, 1H, major rotamer), 4.24 (m, 2H), 4.13 (m, 1H, minor rotamer), 4.04 (m, 1H, minor rotamer), 3.95 (m, 1H, major rotamer), 2.62 (m, 1H, minor rotamer), 2.48 (m, 1H, major rotamer), 2.22 (m, 1H, major rotamer), 2.10 (m, 1H, minor rotamer), 1.07 (m, 2H), 0.07 (m, 9H)

(xxi) Ph(3-Cl)(5-OCHF$_2$)—(R)CH(OH)C(O)—(S)Aze-Pab(2,6-diF)

Ph(3-Cl)(5-OCHF$_2$)—(R)CH(OH)C(O)—(S)Aze-Pab(2,6-diF)(Teoc) (81 mg, 0.127 mmol; see step (xx) above) was dissolved in 0.5 mL of methylene chloride and cooled on an ice bath. TFA (3 mL) was added and the reaction was left for 75 min. The TFA was evaporated and the residue was freeze dried from water and acetonitrile. The crude product was purified by preparative RPLC with CH$_3$CN:0.1M NH$_4$OAc (35:65) to produce 39 mg (55%) of the title compound as its HOAc salt, purity: 99%.

$^1$H NMR (400 MHz, CD$_3$OD mixture of rotamers) δ 7.5–7.4 (m, 2H), 7.32 (m, 1H, major rotamer), 7.28 (m, 1H, minor rotamer), 7.2–7.1 (m, 3H) 6.90 (t, 1H, major rotamer), 6.86 (t, minor rotamer), 5.15 (s, 1H, major rotamer), 5.14 (m, 1H, minor rotamer), 5.07 (s, 1H, minor rotamer), 4.72 (m, 1H, major rotamer), 4.65–4.45 (m, 2H), 4.30 (m, 1H, major rotamer), 4.16 (m, 1H, major rotamer), 4.03 (m, 1H, minor rotamer), 3.95 (m, 1H, minor rotamer), 2.63 (m;, 1H, minor rotamer), 2.48 (m, 1H, major rotamer), 2.21 (m, 1H, major rotamer), 2.07 (m, 1H, minor rotamer), 1.89 (s, 3H) $^{13}$C-NMR (75 MHz; CD$_3$OD): (carbonyl and/or amidine carbons, mixture of rotamers) δ 171.9, 171.2, 165.0, 162.8, 160.4; APCI-MS: (M+1)=503/505 m/z.

EXAMPLE 2

Ph(3-Cl)(5-OCHF$_2$)—(R)CH(OH)C(O)—(S)Aze-Pab(2,6-diF)(OMe)

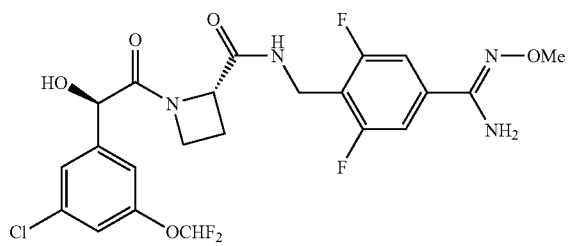

(i) Ph(3-Cl)(5-OCHF$_2$)—(R)CH(OH)C(O)—(S)Aze-Pab(2,6-diF)(OMe,Teoc)

A mixture of Ph(3-Cl)(5-OCHF$_2$)—(R)CH(OH)C(O)—(S)Aze-Pab(2,6-diF)(Teoc) (64 mg, 0.099 mmol; see Example 1(xx) above) and O-methyl hydroxylamine hydrochloride (50 mg, 0.60 mmol) in 4 mL of acetonitrile was heated at 70° C. for 3 h. The solvent was evaporated and the residue was partitioned between water and EtOAc. The aqueous layer was extracted twice with EtOAc and the combined organic phase was washed with water, dried (Na$_2$SO$_4$) and evaporated. The product could be used without further purification. Yield: 58 mg (87%).

$^1$H NMR (400 MHz, CDCl$_3$) δ 7.90 (bt, 1H), 7.46 (m, 1H), 7.25–6.95 (m, 5H), 6.51, t, 1H), 4.88 (s, 1H), 4.83 (m, 1H), 4.6–4.5 (m, 2H), 4.4–3.9 (m, 4H), 3.95 (s, 3H), 3.63 (m, 1H), 2.67 (m, 1H), 2.38 (m, 1H), 1.87 (broad, 1H), 0.98 (m, 2H), 0.01, s, 9H)

(ii) Ph(3-Cl)(5-OCHF$_2$)—(R)CH(OH)C(O)—(S)Aze-Pab(2,6-diF)(OMe)

Ph(3-Cl)(5-OCHF$_2$)—(R)CH(OH)C(O)—(S)Aze-Pab(2,6-diF)(OMe,Teoc) (58 mg, 0.086 mmol; see step (i) above) was dissolved in 3 mL of TFA, cooled on an ice bath and allowed to react for 2 h. The TFA was evaporated and the residue dissolved in EtOAc. The organic layer was washed twice with aqueous sodium carbonate and water, dried (Na$_2$SO$_4$) and evaporated. The residue was freeze-dried from water and acetonitrile to give 42 mg (92%) of the title compound. Purity: 94%.

$^1$H NMR (300 MHz, CDCl$_3$) δ 7.95 (bt, 1H), 7.2–7.1 (m, 4H), 6.99 (m, 1H), 6.52 (t, 1H), 4.88 (s, 1H), 4.85–4.75 (m, 3H), 4.6–4.45 (m, 2H), 4.29 (broad, 1H), 4.09 (m, 1H), 3.89 (s, 3H), 3.69 (m, 1H), 2.64 (m, 1H), 2.38 (m, 1H), 1.85 (broad, 1H) $^{13}$C-NMR (100 MHz; CDCl$_3$): (carbonyl and/or amidine carbons) δ 172.1, 169.8, 151.9 APCI-MS: (M+1) 533/535 m/z

EXAMPLE 3

Ph(3-Cl)(5-OCHF$_2$)—(R)CH(OH)C(O)—(S)Aze-Pab(2,6-diF)(OH)

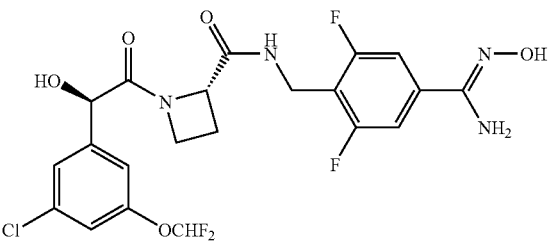

(i) Boc-(S)Aze-NHCH$_2$-Ph(2,6-diF, 4-CN)

Boc-(S)Aze-OH (1.14 g, 5.6 mmol) was dissolved in 45 mL of DMF. 4-Aminomethyl-2,6-difluorobenzonitrile (1.00 g, 5.95 mol, see Example 1(xiv) above), PyBOP (3.10 g, 5.95 mmol) and DIPEA (3.95 mL, 22.7 mmol) were added and the solution was stirred at room temperature for 2 h. The solvent was evaporated and the residue was partitioned between H$_2$O and EtOAc (75 mL each). The aqueous phase was extracted with 2×50 mL EtOAc and the combined organic phase was washed with brine and dried over Na$_2$SO$_4$. Flash chromatography (SiO$_2$, EtOAc/heptane (3/1)) yielded the sub-title compound (1.52 g, 77%) as an oil which crystallized in the refrigerator.

$^1$H-NMR (400 MHz; CD$_3$OD): δ 7.19 (m, 2H), 4.65–4.5 (m, 3H), 3.86 (m, 1H), 3.73 (m, 1H), 2.45–2.3 (m, 2H), 1.39 (s, 9H)

(ii) H-(S)Aze-NHCH$_2$-Ph(2,6-diF, 4-CN)×HCl

Boc-(S)Aze-NHCH$_2$-Ph(2,6-diF, 4-CN) (0.707 g, 2.01 mmol, see step (i) above) was dissolved in 60 mL of EtOAc saturated with HCl(g). After stirring at room temperature for 15 minutes, the solvent was evaporated. The residue was dissolved in CH$_3$CN/H$_2$O (1/1) and was freeze-dried to give the sub-title compound (0.567 g, 98%) as an off-white amorphous powder.

$^1$H-NMR (400 MHz; CD$_3$OD): δ 7.49 (m, 2H), 4.99 (m, 1H), 4.58 (m, 2H), 4.12 (m, 1H), 3.94 (m, 1H), 2.80 (m, 1H), 2.47 (m, 1H) MS (m/z) 252.0 (M+1)$^+$ (iii) Ph(3-Cl)(5-OCHF$_2$)—(R)CH(OH)C(O)—(S)Aze-NHCH$_2$_Ph(2,6-diF, 4-CN)

Ph(3-Cl)(5-OCHF$_2$)—(R)CH(OH)C(O)OH (0.40 g, 1.42 mmol, see Example 1(viii) above) was dissolved in 10 mL of DMF and H-(S)Aze-NHCH$_2$-Ph(2,6-diF, 4-CN)×HCl (0.43 g, 1.50 mmol, see step (ii) above) and PyBOP (0.779 g, 1.50 mmol) were added, followed by DIPEA (1.0 mL, 5.7 mmol). After stirring at room temperature for 2 h, the solvent was is evaporated. The residue was partitioned between H$_2$O (200 mL) and EtOAc (75 mL). The aqueous phase was extracted with 2×75 mL EtOAc and the combined organic phase was washed with brine and dried over Na$_2$SO$_4$. Flash chromatography (SiO$_2$, EtOAc/heptane (4/1)) yielded the sub-title compound (0.56 g, 81%) as an oil.

$^1$H-NMR (400 MHz; CD$_3$OD) rotamers: δ 7.43 (m, 2H), 7.31 (m, 1H, major rotamer), 7.26 (m, 1H, minor rotamer), 7.2–7.1 (m, 2H), 6.90 (t, 1H, major rotamer), 6.86 (t, 1H, minor rotamer), 5.14 (s, 1H, major rotamer), 5.11 (m, 1H, minor rotamer), 5.04 (s, 1H, minor rotamer), 4.71 (m, 1H, major rotamner), 4.6–4.45 (m, 2H), 4.30 (m, 1H, major rotamer), 4.2-3.9 (m, 1H; and 1H, minor rotamer), 2.62 (m, 1H, minor rotamer), 2.48 (m, 1H, major rotamer), 2.21 (m, 1H, major rotamer), 2.09 (m, 1H, minor rotamer) $^{13}$C-NMR (100 MHz; CD$_3$OD): (carbonyl carbons) δ 171.9, 171.8; MS (m/z) 484.0, 485.9 (M−1)$^-$, 486.0, 487.9 (M+1)$^+$ (iv) Ph(3-Cl)(5-OCHF$_2$)—(R)CH(OH)C(O)—(S) Aze-Pab(2,6-diF)(OH)

Ph(3-Cl)(5-OCHF$_2$)—(R)CH(OH)C(O)—(S)Aze-NHCH$_2$-Ph(2,6-diF, 4-CN) (0.555 g, 1.14 mmol, from step (iii) above) was dissolved in 10 mL of EtOH. (95%). To this solution was added hydroxylamine hydrochloride (0.238 g, 3.42 mmol) and Et$_3$N (0.48 mL, 3.44 mmol). After stirring at room temperature for 14 h, the solvent was removed and the residue was dissolved in EtOAc. The organic phase was washed with brine and H$_2$O and was dried over Na$_2$SO$_4$. The crude product was purified by preparative to RPLC with CH$_3$CN:0.1 M NH$_4$OAc as eluent, yielding the title compound as an amorphous powder (0.429 g, 72%) after freeze-drying.

$^1$H-NMR (400 MHz; CD$_3$OD) rotamers: δ 7.35–7.1 (m, 5H), 6.90 (t, 1H, major rotamer), 6.85 (t, 1H, minor rotamer), 5.15 (s, 1H, major rotamer), 5.12 (m, 1H, minor rotamer), 5.08 (s, 1H, minor rotamer), 4.72 (m, 1H, major rotamer), 4.6–4.4 (m, 2H), 4.30 (m, 1H, major rotamer), 4.12 (m, 1H, major rotamer), 4.04 (m, 1H, minor rotamer), 3.94 (m, 1H, minor rotamer), 2.62 (m, 1H, minor rotamer), 2.48 (m, 1H, major rotamer), 2.22 (m, 1H, major rotamer), 2.10 (m, 1H, minor rotamer) $^{13}$C-NMR (100 MHz; CD$_3$OD): (carbonyl and amidine carbons, rotamers) δ 172.4, 171.9, 171.0, 152.3, 151.5 MS (m/z) 517.1, 519.0 (M−1)$^-$, 519.1, 521.0 (M+1)$^+$

EXAMPLE 4

The title compound of Example 1 was tested in Test A above and was found to exhibit an IC$_{50}$TT value of less than 0.02 μM.

EXAMPLE 5

The title compound of Example 1 was tested in Test D above and was found to exhibit an IC$_{50}$ APTT value of less than 1 μM.

EXAMPLE 6

The title compound of Example 2 was tested in Test E above and was found to exhibit oral and/or parenteral bioavailability in the rat as the corresponding active inhibitor (free amidine).

EXAMPLE 7

The title compound of Example 2 was tested in Test G above and was found to be converted to the corresponding active inhibitor (free amidine) in liver microsomes from humans and from rats.

ABBREVIATIONS

Ac=acetyl
APCI=atmospheric pressure chemical ionisation (in relation to MS)
API=atmospheric pressure ionisation (in relation to MS)
aq.=aqueous
AUC=area under the curve
Aze=azetidine-2-carboxylate
AzeOH=azetidine-2-carboxylic acid
Boc=tert-butyloxycarbonyl
BSA=bovine serum albumin
CI=chemical ionisation (in relation to MS)
d=day(s)
DCC=dicyclohexyl carbodiimide
DIBAL-H=di-isobutylaluminium hydride
DIPEA=diisopropylethylamine
DMAP=4-(N,N-dimethyl amino)pyridine
DMF=dimethylformamide
DMSO=dimethylsulfoxide
DVT=deep vein thrombosis
EDC=1-(3-dimethylaminopropyl)-3-ethylcarbodiimide hydrochloride
Et=ethyl
ether=diethyl ether
EtOAc=ethyl acetate
EtOH=ethanol
Et$_2$O=diethyl ether
h=hour(s)
HATU=O-(azabenzotriazol-1-yl)-N,N,N',N'-tetramethyluronium hexafluorophosphate
HBTU=[N,N,N',N'-tetramethyl-O-(benzotriazol-1-yl)uronium hexafluorophosphate]
HCl=hydrochloric acid, hydrogen chloride gas or hydrochloride salt (depending on context)
Hex=hexanes
HOAc=acetic acid or acetic acid salt
HPLC=high performance liquid chromatography
LC=liquid chromatography
Me=methyl
MeOH=methanol
min=minute(s)
MS=mass spectroscopy
MTBE=methyl tert-butyl ether
NADH=nicotinamide adenine dinucleotide, reduced form
NADPH=nicotinamide adenine dinucleotide phosphate, reduced form
NIH=National Institute of Health (US)
NIHU=National Institute of Health units
NMR=nuclear magnetic resonance
OAc=acetate
Pab=para-amidinobenzylamino
H-Pab=para-amidinobenzylamine
Ph=phenyl
PyBOP=(benzotriazol-1-yloxy)tripyrrolidinophosphonium hexafluorophosphate
QF=tetrabutylammonium fluoride RPLC=reverse phase high performance liquid chromatography
rt/RT=room temperature
SOPs=standard operating procedures
TBTU=[N,N,N',N'-tetramethyl-O-(benzotriazol-1-yl)uronium tetrafluoroborate]
TEA=triethylamine
Teoc=2-(trimethylsilyl)ethoxycarbonyl
TEMPO=2,2,6,6-tetramethyl-1-piperidinyloxy free radical
TFA=trifluoroacetic acid
THF=tetrahydrofuran
TLC=thin layer chromatography
UV=ultraviolet Prefixes n, s, i and t have their usual meanings: normal, secondary, iso and tertiary. The prefix c means cyclo.

The invention claimed is:

1. A compound Ph(3-Cl)(5-OCHF$_2$)—(R)CH(OH)C(O)—(S)Aze-Pab(2,6-diF)(OH) or a pharmaceutically-acceptable salt thereof.

2. A pharmaceutical formulation including a compound as defined in claim 1, or a pharmaceutically acceptable salt thereof, in admixture with a pharmaceutically acceptable adjuvant, diluent or carrier.

3. A method of treatment of thrombosis, which method comprises administration of a therapeutically effective amount of a compound as defined in claim 1, or a pharmaceutically acceptable salt thereof, to a person suffering from, or susceptible to, such a condition.

4. A method of treatment of hypercoagulability in blood and/or tissues, which method comprises administration of a therapeutically effective amount of a compound as defined in claim 1, or a pharmaceutically acceptable salt thereof, to a person suffering from, or susceptible to, such a condition.

5. A process for the preparation of a compound of claim 1:
or a pharmaceutically-acceptable salt thereof, which comprises:

(a) reaction of a compound of formula II:

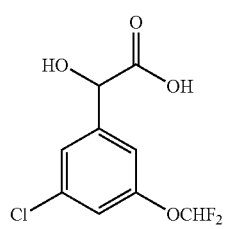

II with a compound of formula XIV,

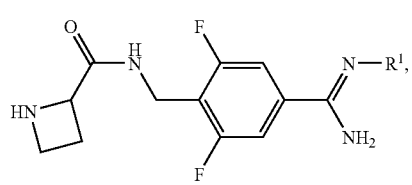

XIV wherein R$^1$ represents OH;

(b) reaction of a compound of formula IV:

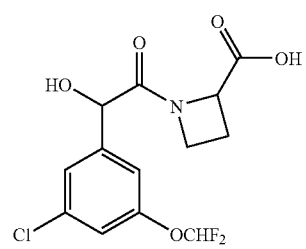

IV with a compound of formula XV,

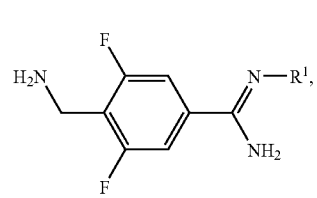

XV wherein R$^1$ represents OH;

(c) reaction of a compound of formula XVI,

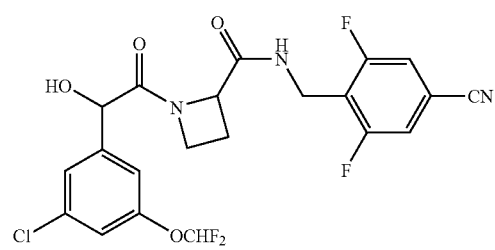

XVI with hydroxylamine;

(d) reaction of a compound of formula XVII,

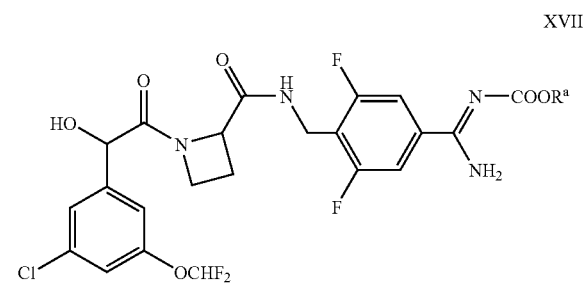

XVII wherein R$^a$ represents —CH$_2$CH$_2$—Si(CH$_3$)$_3$ or benzyl, or a tautomer thereof, with hydroxylamine, or an acid addition salt thereof, followed by removal of the —C(O)OR$^a$ group;

(e) reaction of a compound of formula XVII, as defined above, in which R$^a$ represents benzyl, with hydroxylamine, or an acid addition salt thereof.

* * * * *